United States Patent [19]

Jasys

[11] Patent Number: 5,321,020
[45] Date of Patent: Jun. 14, 1994

[54] ANTIBACTERIAL 2-CARBAPENEM DERIVATIVES

[75] Inventor: Vytautas J. Jasys, New London, Conn.

[73] Assignee: Pfizer Inc., New York, N.Y.

[21] Appl. No.: 768,519

[22] PCT Filed: Mar. 28, 1989

[86] PCT No.: PCT/US89/01281
§ 371 Date: Sep. 24, 1991
§ 102(e) Date: Sep. 24, 1991

[51] Int. Cl.$^5$ .................. C07D 487/04; A61K 31/40
[52] U.S. Cl. .................... 514/210; 540/350; 540/310
[58] Field of Search ............. 540/350, 310; 514/210

[56] References Cited

U.S. PATENT DOCUMENTS

| | | | |
|---|---|---|---|
| 4,619,924 | 11/1984 | Hamanaka | 540/350 |
| 4,665,169 | 5/1987 | Martel et al. | 540/350 |
| 4,739,047 | 4/1988 | Volkmann et al. | 540/310 |
| 4,757,066 | 7/1988 | Shiokari et al. | 514/210 |

FOREIGN PATENT DOCUMENTS 0260042 3/1988 European Pat. Off. .
WO8808845 11/1988 World Int. Prop. O. .

OTHER PUBLICATIONS

Chemical Abstracts vol. 115; 182945K (1991).
Chemical Abstracts vol. 114; 81420J (1991).
Miyadera T., et al., "Synthesis and In Vitro Activity of a New Carbapenem", Journal of Antibiotics, vol. 36, No. 8, 1983 pp. 1034–1038.

*Primary Examiner*—Nicholas S. Rizzo
*Attorney, Agent, or Firm*—Peter C. Richardson; Mervin E. Brokke; Gregg C. Benson

[57] ABSTRACT

Antibacterial compounds of the formula

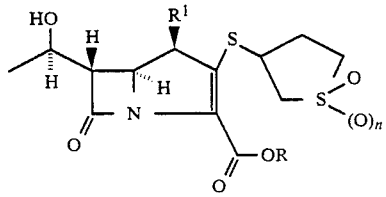

wherein n is 0 or 1, R is hydrogen or a radical forming an ester hydrolyzable under physiological conditions, and $R^1$ is hydrogen or methyl; the pharmaceutically-acceptable cationic salts thereof when R is hydrogen; pharmaceutical compositions thereof; a method of treating bacterial infections therewith; and intermediates useful in the synthesis of said compounds.

21 Claims, No Drawings

ANTIBACTERIAL 2-CARBAPENEM DERIVATIVES

BACKGROUND OF THE INVENTION

The present invention is directed to antibacterial 5R,6S-6-(1R-hydroxyethyl)-2-(3-thiolanyl)thio-2-carbapenem-3-carboxylic acids, as depicted by the for below; the pharmaceutically-acceptable salts and in vivo hydrolyzable esters thereof; and intermediates useful in the preparation of said compounds.

There are numerous reports in the literature concerning antibacterial 2-(alkylthio)-2-carbapenems and related compounds. See, for example, Andrus et al , J. Am. Chem. Soc., vol. 106, pp. 1808-1811, 1984; Afonso et al., ibid., vol. 104, pp. 6139-6140, 1982; DiNinno et al., Tetrahedron Letters, vol. 23, pp. 3535-3538 (1982); Ganguly et al., J. Antimicrobial Chemotherapy, vol. 9, suppl. C, pp. 1-5 (1982); Ghosez et al., Tetrahedron, vol. 39, pp. 2493-2503, 1983; Girijavallabhan et al., J. Antibiotics, vol. 39, pp. 1182-1190, 1986; Girijavallabhan et al., Tetrahedron Letters, vol. 24, pp. 3179-3182, 1979; Leanza et al., Tetrahedron, vol. 39, pp. 2505-2513, 1983; and Shih et al., Heterocycles, vol. 21, pp. 29-40, 1984.

In addition, antibacterial 5R, 6S-6-(1R-hydroxyethyl)-2-(cis-1-oxo-3-thiolanylthio)-2-penem-3-carboxylic acid and 5R,6S-6-(1R-hydroxyethyl)-2-(1,1-dioxo-3thiolanylthio)-2-penem-3-carboxylic acid have been disclosed by Hamanaka, U.S. Pat. No. 4,619,924. More recently, the preferred diastereoisomer, 5R,6S-6-(1R-hydroxyethyl)-2-(1R-oxo-3S-thiolanylthio)-2-penem-3-acid, was identified by Volkmann in International Application No. PCT/US87/01114, designating inter alia the United States of America, published on Nov. 17, 1988 as WO-88/08845.

SUMMARY OF THE INVENTION

It has now been discovered that carbapenems substituted in analogy to the above-noted penems of Hamanaka and Volkmann are especially valuable antibacterial agents. These novel compounds are of the formula

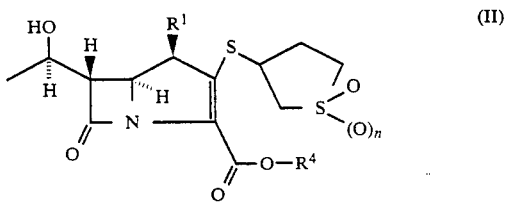

wherein n is 0 or 1; R is hydrogen or a radical forming an ester hydrolyzable under physiological conditions; and $R^1$ is hydrogen or methyl; including the pharmaceutically-acceptable cationic salts thereof when R is hydrogen.

Said pharmaceutically-acceptable cationic salts include, but are not limited to, those of sodium, potassium, calcium, N,N'-dibenzylethylenediamine, N-methylglucamine (meglumine) and diethanolamine. The preferred cationic salts are those of potassium and sodium.

The reference to esters which are hydrolyzable under physiological conditions refers to those esters frequently referred to as "pro-drugs." Such esters are now as well-known and common in the penicillin art as pharmaceutically-acceptable salts. Such esters are generally used to enhance oral absorption, but in any event are readily hydrolyzed in vivo to the parent acid. The more preferred ester forming radicals are those wherein R is:
(5-methyl-1,3-dioxol-2-on-4-yl)methyl;
1H-isobenzofuran-3-on-1-yl;
gamma-butyrolacton-4-yl;
—$CHR^2OCOR^3$; or
—$CHR^2OCOOR^3$;
wherein $R^2$ is hydrogen or methyl; and $R^3$ is ($C_1$-$C_6$)alkyl. The most preferred radicals are pivaloyloxymethyl and 1-(ethoxycarbonyloxy)ethyl.

For ease of preparation, the preferred value of $R^1$ is hydrogen. When n is 0, it is preferred that the groups attached to the thiolane ring be cis to one another, most preferably in the 1R,3S-configuration, i.e.,

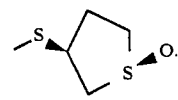

The present invention is also directed to intermediate compounds of the formula

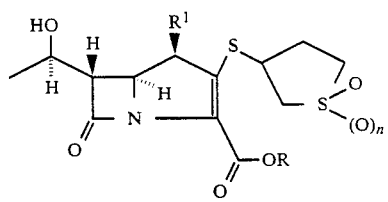

(II)

wherein n is 0 or 1; $R^1$ is hydrogen or methyl, and $R^4$ is a conventional carboxylic acid protecting group such as benzyl, p-nitrobenzyl, or —$CH_2CX$=$CH_2$ where X is H or Cl. For their ease of preparation and the facile removal of the protecting group, the preferred compounds of the formula (II) are those wherein $R^4$ is —$CH_2CX$=$CH_2$, most preferably with X as hydrogen

Detailed Description of the Invention

The antibacterial compounds of the present invention, having the formula (I), are readily and conventionally prepared from the ketonic compound of the formula

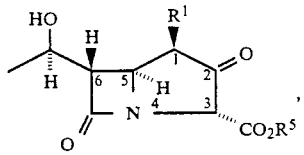

(III)

wherein $R^1$ is as defined above and $R^5$ is a conventional carboxylic acid protecting group or a radical forming an ester hydrolyzable under physiological conditions; and a 3-thiolanyl mercaptan of the formula

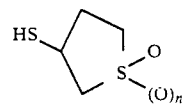

wherein n is as defined above. For example, the ketone (III) is initially reacted with substantially one molar equivalent of a reagent such as diphenyl chlorophosphate, $(C_6H_5O)_2P(O)Cl$, in the presence of substantially one molar equivalent of a hindered tertiary amine such as di(isopropyl)ethylamine to form the enol phosphate ester of the formula

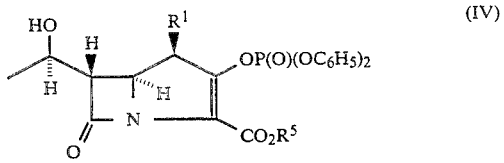

Generally without isolation, with an additional molar equivalent of the amine present, the phosphate (IV) is then reacted directly with substantially one molar equivalent of the appropriate 3-thiolanyl mercaptan, thus forming the intermediate compound of the formula (II) when $R^5$ is a carboxylic acid protecting group such as $CH_2CX=CH_2$, or finished prodrug ester product of the formula (I) when $R^5$ is a radical forming an ester hydrolyzable under physiological conditions. This reaction sequence is generally carried out in a reaction-inert solvent such as acetonitrile. While temperature is not particularly critical, it is preferred to operate in the range of about $-20°$ to $30°$ C., conveniently at ice bath temperature ($0°\cong5°$ C.).

As used herein, the expression "reaction-inert solvent" refers to a solvent which does not interact with starting materials, reagents, intermediates or products in a manner which adversely affects the yield of the desired product.

When the product is an allyl or 2-chloroallyl ester of the formula (II), the ester is hydrolyzed to produce the desired penem of the formula (I), above, in the form of the acid or its pharmaceutically-acceptable cationic salt. Anhydrous conditions are generally employed to avoid any possible degradation of the beta-lactam. Preferred conditions employ 1 to 1.1 molar equivalents of an alkali metal salt of a lipophilic carboxylic acid (e.g., sodium 2-ethylhexanoate) in an anhydrous reaction-inert solvent (e.g., methylene chloride and/or ethyl acetate) in the presence of catalytic amounts of triphenylphosphine and tetrakis(triphenylphosphine)palladium (e.g., about 0.15 molar equivalents of the former and about 0.075 molar equivalents of the latter). This reaction is generally carried out under an inert atmosphere and protected from light. Although temperature is not critical, the reaction is conveniently carried out at ambient temperature. With these reagents, the compound of the formula (I) is usually initially isolated in the form of its alkali metal (e.g., sodium) salt. If desired, the salt is converted to the free acid form, during or after isolation, by standard methods, e.g., acidification of an aqueous solution of the salt, with extraction of the free acid into a water immiscible organic solvent. Alternative carboxylic acid protecting groups are removed by conventional means, e.g., benzyl and p-nitrobenzyl groups by hydrogenation over a noble metal catalyst such as Pd/C.

Other pharmaceutically-acceptable cationic salts of the present invention are also readily prepared by standard methods. For example, an equivalent of the corresponding cationic hydroxide, carbonate or bicarbonate or of an amine, is combined with the carboxylic acid in an organic or aqueous solvent, preferably at reduced temperature (e.g., $0°$–$5°$ C.), with vigorous actuation and slow addition of the base. The salt is isolated by concentration and/or the addition of a non solvent.

The compounds of the formula (I) wherein R represents an in vivo hydrolyzable ester are alternatively prepared from the corresponding free acids or cationic salts according to known methods, readily identified by those skilled in the penicillin art (see for example, U.S. Pat. Nos. 3,951,954; 4,234,579; 4,287,181; 4,342,693; 4,452,796; 4,342,693; 4,348,264; 4,416,891; and 4,457,924). In the present instance, the preferred precursors are generally in the form of a salt, preferably the tetrabutylammonium salt, which is reacted with the appropriate ester forming reagent, e.g., chloromethyl pivalate or 1-chloroethyl ethyl carbonate.

Concerning other starting materials required for the process of the present invention, the ketones of the formula (III) are readily available by literature methods (for example, see the carbapenem references cited above), and by means of preparative methods of the type detailed below. The required mercaptans are available according to above cited Hamanaka and Volkmann.

The in vitro activity of the compounds of the formula (I) is determined by measuring the minimum inhibitory concentration (MIC) of the free acids or cationic salts in mcg/ml against a variety of microorganisms. The procedure which is followed is the one recommended by the International Collaborative Study on Antibiotic Sensitivity Testing (Ericcson and Sherris, *Acta. Pathologica et Microbiologia* Scandinav, Supp. 217, Section B: 64–68 [1971]), and employs brain heart infusion (BHI) agar and the inocula replicating device. Overnight growth tubes are diluted 100 fold for use as the standard inoculum (20,000–10,000 cells in approximately 0.002 ml are placed on the agar surface; 20 ml of BHI agar/dish). Twelve 2 fold dilutions of the test compound are generally employed, with initial concentration of the test drug being 100–200 mcg/ml. Single colonies are disregarded when reading plates after 18 hours at $37°$ C. The susceptibility (MIC) of the test organism is accepted as the lowest concentration of compound capable of producing complete inhibition of growth as judged by the naked eye.

The in vivo activity of the compounds of the formula (I) can be determined by conventional animal protection studies, usually carried out in mice. In this test groups of mice are usually infected intraperitoneally with multiple lethal doses of a microorganism. Each group of mice is dosed, usually orally or subcutaneously, with a particular dose of the anti-bacterial compound. Such in vivo results are generally reported in the form of a $PD_{50}$ value in mg/Kg, i.e., the dose of drug in mg/Kg which will protect 50% of mice from the infecting microorganism. This value is conveniently determined graphically, e.g., by plotting dose against % protection.

The present antibacterial compounds find primary use in animals, including man, in the systemic treatment of infections due to susceptible microorganisms. They are dosed at a level of 2.5–100 mg/kg per day, preferably 5–50 mg/kg/day, in single or divided doses. Variation in dosage will be made depending upon the animal and upon the particular susceptibility of the microorganism. These compounds are dosed orally or parenterally, the preferred route being oral, particularly when the antibiotic is in the form of a prodrug ester, as defined above. The susceptibility of microorganisms isolated in the field is routinely tested in bacteriology laboratories by the well-known disc-plate method. Compound (I) is generally the compound of choice when it shows a relatively large zone of inhibition against the bacteria causing the infection to be treated.

Preparation of optimal dosage forms will be by methods well known in the pharmaceutical art. For oral administration, the compounds are formulated alone or in combination with pharmaceutical carriers such as inert solid diluents, aqueous solutions or various non-toxic organic solvents in such dosage forms as gelatin capsules, tablets, powders, lozenges, syrups and the like. Such carriers include water, ethanol, benzyl alcohol; glycerin, propylene glycol, vegetable oils, lactose, starches, talc, gelatins, gums and other well known carriers. The parenteral dosage forms required for the above systemic use are dissolved or suspended in a pharmaceutically-acceptable carrier such as water, saline, sesame oil and the like. Agents which improve the suspendability and dispersion qualities can also be added.

Based on nothing more than their excellent in vitro activity, the present antibacterial compounds, particularly in free acid or salt form, also find use in the topical treatment of superficial infections in animals, including man, caused by susceptible microorganisms, the compound (I) is formulated by methods well known in the pharmacist's art into lotions, ointments, creams, salves, gels, or the like at concentrations in the range 5-200 mg/cc of the dosage form, preferably in the range 10-100 mg/cc. The dosage form is applied at the site of infection ad libitum, generally at least once a day.

The present invention is illustrated by the following examples. However, it should be understood that the invention is not limited to the specific details of these examples.

EXAMPLE 1

Allyl (5R,6S)-6-(1R-Hydroxyethyl)-2-(1,1-dioxo3-thiolanyl-thio)-2-carbapenem-3-carboxylate (II, n=1, $R^4=CH_2CH=CH_2$)

Under $N_2$, allyl (3R,5R,6S)-6-(1R-hydroxyethyl)2-oxocarbapenam (0.109 g, 0.43 mmol) was dissolved in 10 ml of $CH_3CN$ and cooled to 0°-5° C. Diphenyl chlorophosphate (0.114 g, 0.43 mmol) and then diisopropylethylamine (0.075 ml, 0.43 mmol) were added and the mixture stirred for 30 minutes at 0°-5° C. to form a solution of the intermediate enol phosphate ester of the above formula (IV) wherein $R^5$ is allyl 3-Thiolanyl mercaptan 1,1-dioxide (0.065 g, 0.43 mmol) and a second equivalent of the amine (0.075 ml, 0.43 mmol) were added. After stirring for an additional 1 hour at 0°-5° C., the reaction mixture was poured into 75 ml of ethyl acetate, extracted in sequence with $1\times15$ ml $H_2O$, $2\times15$ ml saturated NaHCO , $1\times15$ ml $H_2O$ and $1\times15$ ml brine, dried ($Na_2SO_4$), stripped of solvent and the residue chromatographed on silica gel using ethyl acetate as eluant to yield 38 mg of present title product, an approximately 1:1 mixture of 3R and 3S-thiolanyl side chain diastereoisomers; TLC Rf 0.2 (ethyl acetate); $^1$H-NMR ($CDCl_3$)delta(ppm) 1.32 (d, 3H), 2.04 (bs, 1H), 2.14-2.26 (m, 1H), 2.57-2.67 (m, 1H), 2.97-3.36 (m, 6H), 3.41-3.51 (m, 1H), 3.76-3.88 (m, 1H), 4.17-4.28 (m, 2H), 4.79 (dd, 2H), 5.24 (d, 1H), 5.41 (d, 1H), 5.86-5.99 (m, 1H); HRMS 387.0765, calcd. 387.0810.

To avoid product loss to the aqueous phases, it is preferable to directly chromatograph the reaction mixture, as in Example 3 below.

EXAMPLE 2

Sodium (5R,6S)-6-(1R-Hydroxyethyl)-2-(1,1-dioxo-3-thiolanyl-thio)-2-carbapenem-3-carboxylate (I, n=1, R=H as the sodium salt)

Under $N_2$ and in a flask wrapped with aluminum foil, title product of the preceding Example (19 mg, 0.05 mmol) was dissolved in 0.5 ml $CH_2Cl_2$. Triphenylphosphine (2.6 mg) and sodium 2-ethylhexanoate 8.3 mg in 0.43 ml of ethyl acetate) were added and the mixture protected from light. Finally tetrakis(triphenylphosphine)palladium (5 mg) was added and the mixture stirred for 45 minutes. Present title product (14.4 mg) was recovered by filtration with ethyl acetate wash; $^1$H-NMR ($D_2O$)delta(ppm) 1.27 (d, 3H), 2.2-2.3 (m, 1H), 2.65-2.69 (m, 1H), 3.11-3.30 (m, 4H), 3.4-3.46 (m, 2H),3.65-3.74 (m, 1H), 4.04-4.23 (m, 4H), 3.4-3.46 (m, 2H),3.65-3.74 (m, 1H), 4.04-4.23 (m, 3(m, 3H) 1R(KBr) includes 1754 cm$^{-1}$.

EXAMPLE 3

Allyl (5R,6S)-6-(1R-Hydroxyethyl)-2-(1R-oxo3S-thiolanyl-thio)-2-carbapenem-3-carboxylate (II, n=0, $R^4=CH_2CH=CH_2$)

With stirring under $N_2$, 3S-(acetylthio)thiolane 1R-oxide (0.712 g, 4 mmol; Volkmann, WO 88/08845) was dissolved in 2.5 ml $H_2O$ and cooled to $-5°$ C. NaOH (0.32 g, 8 mmol) was added, and the mixture warmed to 0°-5° C., stirred for 30 minutes, acidified with 0.8 ml 12N HCl at 5°-10° C., saturated with $Na_2SO_4$ at ambient temperature and extracted $4\times7$ ml $CH_2Cl_2$. The organic extracts were combined, dried ($Na_2SO_4$) and filtered to yield a solution of 3S-thiolanyl mercaptan 1R-oxide used without isolation directly below.

In a separate flask, allyl (3R,5R,6S)-6-(1R-hydroxyethyl)-2-oxocarbapenam (0.506 g, 2 mmol) was converted to a solution of the phosphate ester intermediate and then reacted with said mercaptan solution according to the methods of Example 1. The entire reaction mixture was chromatographed directly on silica gel using 9:1 ethyl acetate:$CH_3OH$ as eluant. The initial product residue was rechromatographed using acetone as eluant to yield 0.428 g of present, purified title product as a foam; TLC Rf 0.1. (4:1 ethyl acetate:$CH_3OH$), 0.25 (acetone); $^1$H-NMR ($CDCl_3$)delta(ppm) 1.3 (d, 3H), 2.59-2.79 (m, 4H), 3.05-3.26 (m, 4H), 3.52-3.58 (m, 1H), 3.74-3.82 (m, 1H), 4.15-4.25 (m, 2H), 4.73 (dd, 2H), 5.27 (d, 1H), 5.40 (d, 1H), 5.86-5.97 (m, 1H).

EXAMPLE 4

Sodium (5R,6S)-6-(1R-Hydroxyethyl)-2-(1R-oxo3S-thiolanyl-thio)-2-carbapenem-3-carboxylate n=O, $R_4$=H as the sodium salt.

By the method of Example 2, title product of the preceding Example (0.34 g, 0.92 mmol) was converted to 0.28 g of present title product.

Further purification was achieved dissolving 0.27 g of this product in 40 ml of water, treating with 0.4 g of activated carbon at 0°-5° C. for 20 minutes, filtering, extracting the filtrate $2\times25$ ml ethyl acetate, and freeze drying the aqueous layer to yield 0.20 g of present, purified title product; $^1$H-NMR (D$_2$O)delta(ppm) 1.26 (d, 3H), 2.41–2.48 (m, 1H), 2.69–2.75 (m, 1H), 2.85–2.90 (m, 1H), 2.91–2.98 (m, 1H), 3.15–3.39 (m, 3H), 3.39 (dd, 1H), 3.82–3.92 (m, 2H), 4.18–4.23 (m, 2H); MS 354 (M+); IR(KBr) includes 1761 cm$^{-1}$.

PREPARATION 1

Allyl 3-Pyrrolidino-2-butenoate

Allyl acetoacetate (68.4 ml, 0.5 mol) was added to pyrrolidine (41.6 ml, 0.5 mol) in 150 ml of toluene. An exotherm was noted. The mixture was heated at reflux for 3 hours, cooled, and stripped of toluene to yield 45 g of title product as a pale yellow oil.

PREPARATION 2

(3S, 4R)-4-[3-(Allyloxycarbonyl)-2-pyrrolidino2-propenyl]-3-[1 R-1-(dimethyl-t-butylsiloxy)ethyl]-2-azetidinone Under N$_2$, title product of the preceding Preparation (9.75 g, 0.05 mol) in 100 ml dry tetrahydrofuran was cooled to −60° C. Maintaining a temperature below −50° C., butyllithium (31 ml of 1.6M in hexanes, 0.051 mol) was added, and the mixture stirred 20 minutes at −60° C. and 30 minutes at 0° C., and then recooled to −60° C. Diethylaluminum chloride (50 ml) was added and stirring continued at −60° C. for 20 minutes, at which time 3R,4R-4-acetoxy-3-[1R-1-(dimethyl-t-butyl-silylyloxy)ethyl]-2-azetidinone (5.74 g, 0.02 mol; Leanza et al., Tetrahedron, vol. 39, pp. 2505–2513, 1983) in 25 ml dry tetrahydrofuran was added, and the mixture further stirred 20 minutes at −60° C. and 30 minutes at 0°–5° C. The reaction mixture was then poured into 400 ml of ice and water and 400 ml of ethyl acetate, filtered to remove insoluble byproducts and the layers separated. The aqueous layer was extracted with 400 ml fresh ethyl acetate and the organic layers were combined, backwashed 4'200 ml H$_2$O and then 1×200 ml brine, dried (Na$_2$SO$_4$) and stripped of solvent. The residue was chromatographed on silica gel using 3:1 hexane:acetone as eluant to yield 4.59 g of present title product; TLC Rf 0.2 (3:1 hexane:acetone).

PREPARATION 3

(3S,4R)-4-[3-(Allyloxycarbonyl)2-oxopropyl]-3-[1R-1-(dimethyl-t-butylsilyloxy) ethyl]-2-azetidinone Title product of the preceding Preparation (4.38 g, 0.0104 mol) was combined with 75 ml tetrahydrofuran, 4 ml acetic acid and 1 ml H$_2$O. After stirring for 24 hours, the mixture was diluted with 250 ml ethyl acetate, washed in sequence with 4 x 50 ml H$_2$O, 2×50 ml saturated NaHCO$_3$, 1×50 ml H$_2$O and 1×50 ml brine, dried (Na$_2$SO$_4$), stripped of solvent, twice restripped from 25 ml of CH$_2$Cl$_2$ and pumped dry in high vacuum to yield 3.8 g of present title product; TLC Rf 0.3 (1:1 hexane:ethyl acetate).

PREPARATION 4

(3S,4R)-4-[3-(Allyloxycarbonyl) 2-oxopropyl]-3-[1R-1-hydroxyethyl]-2-azetidinone Title product of the preceding Preparation (0.82 g, 2.2 mmol) was dissolved in 15 ml CH$_3$OH and cooled to 0°–5° C. with stirring. 6N HCl (1.5 ml, 9 mmol) was added and the mixture allowed to warm to room temperature and, after stirring for 2 hours, poured into 25 ml of water and neutralized [pH 7) with 2% NaHCO$_3$. The mixture was then saturated with NaCl and extracted 4×30 ml CH$_2$Cl$_2$. The extracts were combined, dried (Na$_2$SO$_4$), stripped of solvent, and the residue chromatographed on silica gel using 19:1 ethyl acetate:CH$_3$OH as eluant to yield 0.38 g of present title product; TLC Rf 0.2 (ethyl acetate).

PREPARATION 5

(3S,4R)-4-[3-(Allyloxycarbonyl) 3-diazo-2-oxopropyl]-3-[1R-hydroxyethyl-2-azetidinone By the method of Ratcliffe et al., Tetrahedron Letters, vol. 21, pp. 31–34, title product of the preceding Preparation (0.38 g, 1.5 mmol) in 15 ml of CH$_3$CN at 0°–5° C. under N$_2$ was reacted with p-carboxybenzenesulfonylazide (0.34 g, 1.5 mmol) in the presence of triethylamine (0.41 ml, 3 mmol). The reaction mixture was warmed to room temperature, stirred for 30 minutes, filtered, and the filtrate stripped of solvent. The residue was pumped dry to yield present title product; TLC Rf 0.33 (ethyl acetate); all of which was used in the next step.

PREPARATION 6

Allyl (3R,5R,6S)-6-(1R-Hydroxyethyl)-2-oxocarbapenam (III, R$^5$=CH$_2$CH=CH$_2$)

Under N$_2$, the entire product of the preceding Preparation (1.5 mmol) was taken into 50 ml of C$_6$H$_6$. Rh$_2$(CH$_3$CO$_4$ (25 mg) was added and the mixture heated to reflux for 12 minutes, then cooled, filtered on a millipore filter and the filtrate stripped of solvent. The semisolid residue was triturated and restripped to a second residue which was chromatographed on silica gel using 19:1 ethyl acetate:CH3OH as eluant to yield 0.285 g of present title product as an oil. Trituration with ether gave 0.119 g of crystalline title product; TLC Rf 0.6 (ethyl acetate).

This Preparation was repeated using only 4.2 ml of C$_6$H$_6$ with 12.6 ml of ethyl acetate as cosolvent to yield 0.142 g of present title product from the ether trituration, and an additional 0.054 g by concentration of the ether mother liquor.

I claim:

1. A compound having the formula

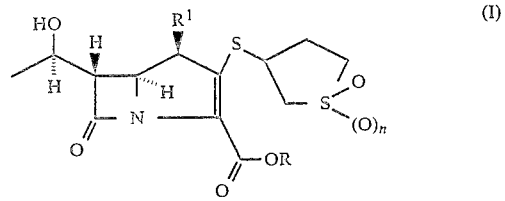

wherein n is 0 or 1; R is hydrogen or a radical forming an ester hydrolyzable under physiological conditions; and R$^1$ is hydrogen or methyl; or a pharmaceuticallyacceptable cationic salt thereof when R is hydrogen.

2. A compound of claim 1 wherein R$^1$ is hydrogen.
3. A compound of claim 2 wherein R is hydrogen.
4. The compound of claim 3 wherein n is 1.
5. A compound of claim 3 wherein n is 0.
6. A compound of claim 5 wherein the groups attached to the thiolane ring are cis to one another.
7. The compound of claim 6 wherein configurations on the thiolane ring are 1R,3S, i.e.,

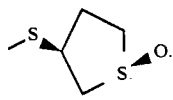

8. A compound of claim 2 wherein R is a radical group forming an ester hydrolyzable under physiological conditions.

9. A compound of claim 8 wherein R is:
(5-methyl-1,3-dioxol-2-on-4-yl)methyl;
1H-isobenzofuran-3-on-1-yl;
gamma-butyrolacton-4-yl;
—CHR²OCOR³; or
—CHR²OCOOR³;
wherein R² is hydrogen or methyl; and R³ is $(C_1-C_6)$alkyl.

10. A compound of claim 9 wherein R is 1-(ethoxycarbonyloxy)ethyl.

11. A compound of claim 9 wherein R is pivaloyloxymethyl.

12. A pharmaceutical composition comprising an antibacterial amount of a compound of claim 1 and a pharmaceutically-acceptable carrier.

13. A method of treating a bacterial infection in a mammal which comprises administering to said mammal an antibacterial amount of a compound of claim 1.

14. A compound having the formula

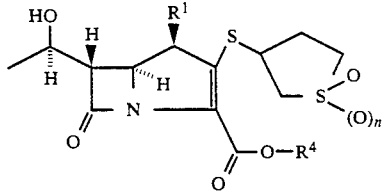

wherein n is 0 or 1, $R^1$ is hydrogen or methyl, and $R^4$ is a conventional carboxylic acid protecting group.

15. A compound of claim 14 wherein $R^1$ is hydrogen.

16. A compound of claim 15 wherein $R^4$ is —CH₂CX=CH₂, and X is hydrogen or chloro.

17. A compound of claim 16 wherein X is hydrogen.

18. The compound of claim 17 wherein n is 1.

19. A compound of claim 17 wherein n is 0.

20. A compound of claim 19 wherein the groups attached to the thiolane ring are cis to one another.

21. The compound of claim 20 wherein configurations on the thiolane ring are 1R,3S, i.e.,

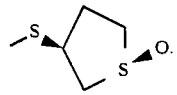

* * * * *